(12) United States Patent  
Dharmadhikary et al.

(10) Patent No.: US 8,137,790 B2
(45) Date of Patent: Mar. 20, 2012

(54) NONWOVEN MEDICAL FABRIC

(75) Inventors: Rahul Dharmadhikary, South Windsor, CT (US); Rongguo Zhao, Simsbury, CT (US)

(73) Assignee: Ahlstrom Corporation, Helsinki (FI)

( * ) Notice: Subject to any disclaimer, the term of this patent is extended or adjusted under 35 U.S.C. 154(b) by 501 days.

(21) Appl. No.: 12/280,016

(22) PCT Filed: Feb. 21, 2007

(86) PCT No.: PCT/FI2007/050089
§ 371 (c)(1), (2), (4) Date: Dec. 11, 2008

(87) PCT Pub. No.: WO2007/096470
PCT Pub. Date: Aug. 30, 2007

(65) Prior Publication Data
US 2009/0169827 A1    Jul. 2, 2009

Related U.S. Application Data

(60) Provisional application No. 60/775,392, filed on Feb. 21, 2006.

(51) Int. Cl.
B32B 5/14    (2006.01)
B32B 3/00    (2006.01)
A61B 19/08   (2006.01)

(52) U.S. Cl. ........ 428/172; 428/156; 428/170; 428/171; 428/198; 128/853; 128/854; 128/849

(58) Field of Classification Search .................. 428/156, 428/170, 171, 172, 198; 128/849, 852, 853, 128/854; 264/167, 173.1, 175, 257, 258, 264/284, 293, 320, 324
See application file for complete search history.

(56) References Cited

U.S. PATENT DOCUMENTS

| 5,599,420 A | 2/1997 | Yeo et al. |
| 6,468,931 B1 | 10/2002 | Reeder et al. |
| 2004/0209541 A1 | 10/2004 | Bonneh |

FOREIGN PATENT DOCUMENTS

| EP | 0 683 260 A2 | 11/1995 |
| WO | WO 93/25746 A1 | 12/1993 |
| WO | WO 98/56304 A1 | 12/1998 |
| WO | WO 03/049937 A1 | 6/2003 |

OTHER PUBLICATIONS

International Search Report mailed May 30, 2007.

*Primary Examiner* — Catherine A Simone
(74) *Attorney, Agent, or Firm* — Nixon & Vanderhye P.C.

(57) ABSTRACT

A method of manufacturing a nonwoven fabric including at least one nonwoven web material layer having thermoplastic polymer filaments and an initial thickness Ts, wherein the method includes embossing the nonwoven web material layer to form in the layer an embossed portion having a compressed thickness Tc that is less than Ts and an expanded portion of the layer having a thickness Te that is greater than Ts.

31 Claims, 5 Drawing Sheets

NONWOVEN MEDICAL FABRIC

CROSS RELATED APPLICATION

This application is the US national phase of international application PCT/FI2007/050089 filed 21 Feb. 2007 which designated the U.S. and claims benefit of U.S. patent application Ser. No. 60/775,392 filed 21 Feb. 2006, the entire contents of these applications are hereby incorporated in their entireties by reference.

FIELD OF THE INVENTION

Briefly, the present invention relates generally to a new and improved nonwoven medical fabric advantageously used for medical gowns, medical drapes and medical drapes with a fenestration.

BACKGROUND OF THE INVENTION

Medical drapes may define a fenestration or window through which a surgical procedure can be performed. Such drapes can comprise a fenestration material surrounding some or all of the fenestration. The fenestration material provides an absorptive reservoir for fluids released at the surgical site.

Conventionally, nonwoven web materials comprising cellulosic staple fibers have been used as a fenestration material. The cellulosic fiber containing nonwovens have excellent absorbent properties. However the cellulosic fiber containing nonwovens exhibit undesirable properties such as linting and high flammability.

Hydrophilically treated spunbond nonwoven materials have also been used for medical drapes. However, known Hydrophilically treated spunbond nonwoven materials are not embossed and typically provide limited absorbency and perception.

DEFINITIONS

Bicomponent fiber or filament—Conjugate fiber or filament that has been formed by extruding polymer sources from separate extruders and spun together to form a single fiber or filament. Typically, two separate polymers are extruded, although a bicomponent fiber or filament may encompass extrusion of the same polymeric material from separate extruders. The extruded polymers are arranged in substantially constantly positioned distinct zones across the cross-section of the bicomponent fibers or filaments and extend substantially continuously along the length of the bicomponent fibers or filaments. The configuration of bicomponent fibers or filaments can be symmetric (e.g., sheath:core or side:side) or they can be asymmetric (e.g., offset core within sheath; crescent moon configuration within a fiber having an overall round shape). The two polymer sources may be present in ratios of, for example (but not exclusively), 75/25, 50/50 or 25/75.

Conjugate fiber or filament—Fiber or filament that has been formed by extruding polymer sources from separate extruders and spun together to form a single fiber or filament. A conjugate fiber encompasses the use of two or more separate polymers each supplied by a separate extruder. The extruded polymers are arranged in substantially constantly positioned distinct zones across the cross-section of the conjugate fiber or filament and extend substantially continuously along the length of the conjugate fiber or filament. The shape of the conjugate fiber or filament can be any shape that is convenient to the producer for the intended end use, e.g., round, trilobal, triangular, dog-boned, flat or hollow.

Cross machine direction (CD)—The direction perpendicular to the machine direction.

Denier—A unit used to indicate the fineness of a filament given by the weight in grams for 9,000 meters of filament. A filament of 1 denier has a mass of 1 gram for 9,000 meters of length.

Extruded web material—A nonwoven sheet material formed by the spunbond or meltblown process. As used herein an extruded web material excludes nonwoven web materials made from staple fibers using wet laid, air laid or carding processes. The extruded web material can comprise one or more layers and can comprise post-formation treatments.

Fiber—A material form characterized by an extremely high ratio of length to diameter. As used herein, the terms fiber and filament are used interchangeably unless otherwise specifically indicated.

Filament—A substantially continuous fiber. As used herein, the terms fiber and filament are used interchangeably unless otherwise specifically indicated.

Machine direction (MD)—The direction of travel of the forming surface onto which fibers or filaments are deposited during formation of a nonwoven web material.

Meltblown fiber—A fiber formed by extruding a molten thermoplastic material as filaments from a plurality of fine, usually circular, die capillaries into a high velocity gas (e.g., air) stream which attenuates the filaments of molten thermoplastic material to reduce their diameter. Thereafter, the meltblown fibers are carried by the high velocity gas stream and are deposited on a collecting surface to form a web of randomly dispersed meltblown fibers. Meltblown fibers are generally continuous. The meltblown process includes the melt-spray process.

Non-thermoplastic polymer—Any polymer material that does not fall within the definition of thermoplastic polymer.

Nonwoven fabric, sheet or web—A material having a structure of individual fibers which are interlaid, but not in an identifiable manner as in a woven or knitted fabric. Nonwoven materials have been formed from many processes such as, for example, meltblowing, spunbonding, carding and water laying processes. The basis weight of nonwoven fabrics is usually expressed in grams per square meter (gsm) and the fiber fineness is measured in denier.

Perception—The subjective three dimensional effect or three dimensional appearance of a sample.

Polymer—A long chain of repeating, organic structural units. Generally includes, for example, homopolymers, copolymers, such as for example, block, graft, random and alternating copolymers, terpolymers, etc, and blends and modifications thereof. Furthermore, unless otherwise specifically limited, the term polymer includes all possible geometrical configurations. These configurations include, for example, isotactic, syndiotactic and random symmetries.

Spunbond filament—A filament formed by extruding molten thermoplastic materials from a plurality of fine, usually circular, capillaries of a spinneret. The diameter of the extruded filaments is then rapidly reduced as by, for example, eductive drawing and/or other well-known spunbonding mechanisms. Spunbond fibers are generally continuous with deniers within the range of about 0.1 to 5 or more.

Spunbond nonwoven web—Webs formed (usually) in a single process by extruding at least one molten thermoplastic material as filaments from a plurality of fine, usually circular, capillaries of a spinneret. The filaments are partly quenched and then drawn out to reduce fiber denier and increase molecular orientation within the fiber. The filaments are generally continuous and not tacky when they are deposited onto a collecting surface as a fibrous batt. The fibrous batt is then bonded by, for example, thermal bonding, chemical binders, mechanical needling, hydraulic entanglement or combinations thereof, to produce a nonwoven fabric.

Staple fiber—A fiber that has been formed at, or cut to, staple lengths of generally one quarter to eight inches (0.6 to 20 cm). Staple fibers and the use of staple fibers are not encompassed by the present invention.

Substantially continuous—in reference to the polymeric filaments of a nonwoven web, it is meant that a majority of the filaments or fibers formed by extrusion through orifices remain as continuous nonbroken filaments as they are drawn and then impacted on the collection device. Some filaments may be broken during the attenuation or drawing process, with a substantial majority of the filaments remaining continuous.

Tex—A unit used to indicate the fineness of a filament given by the weight in grams for 1,000 meters of filament. A filament of 1 tex has a mass of 1 gram for 1,000 meters of length.

Thermoplastic polymer—A polymer that is fusible, softening when exposed to heat and returning generally to its unsoftened state when cooled to room temperature. Thermoplastic materials include, for example, polyvinyl chlorides, some polyesters, polyamides, polyfluorocarbons, polyolefins, some polyurethanes, polystyrenes, polyvinyl alcohol, copolymers of ethylene and at least one vinyl monomer (e.g., poly (ethylene vinyl acetates), and acrylic resins.

SUMMARY OF THE INVENTION

A primary object of the present invention is to provide a nonwoven medical fabric, which is able to avoid some or all of the drawbacks of the prior art medical fabrics.

Another object of the invention is to apply embossing treatment to hydrophilically treated spunbond nonwoven materials to improve their absorbency and perception.

Abovementioned objects of the invention are achieved by the characterizing features of claim 1.

Other characterizing features of the invention have been discussed in more detail in the appended claims.

BRIEF DESCRIPTION OF THE DRAWINGS

Referring now to the drawings wherein like elements are numbered alike in the several Figures.

DESCRIPTION OF THE PREFERRED EMBODIMENTS

Figure 1:
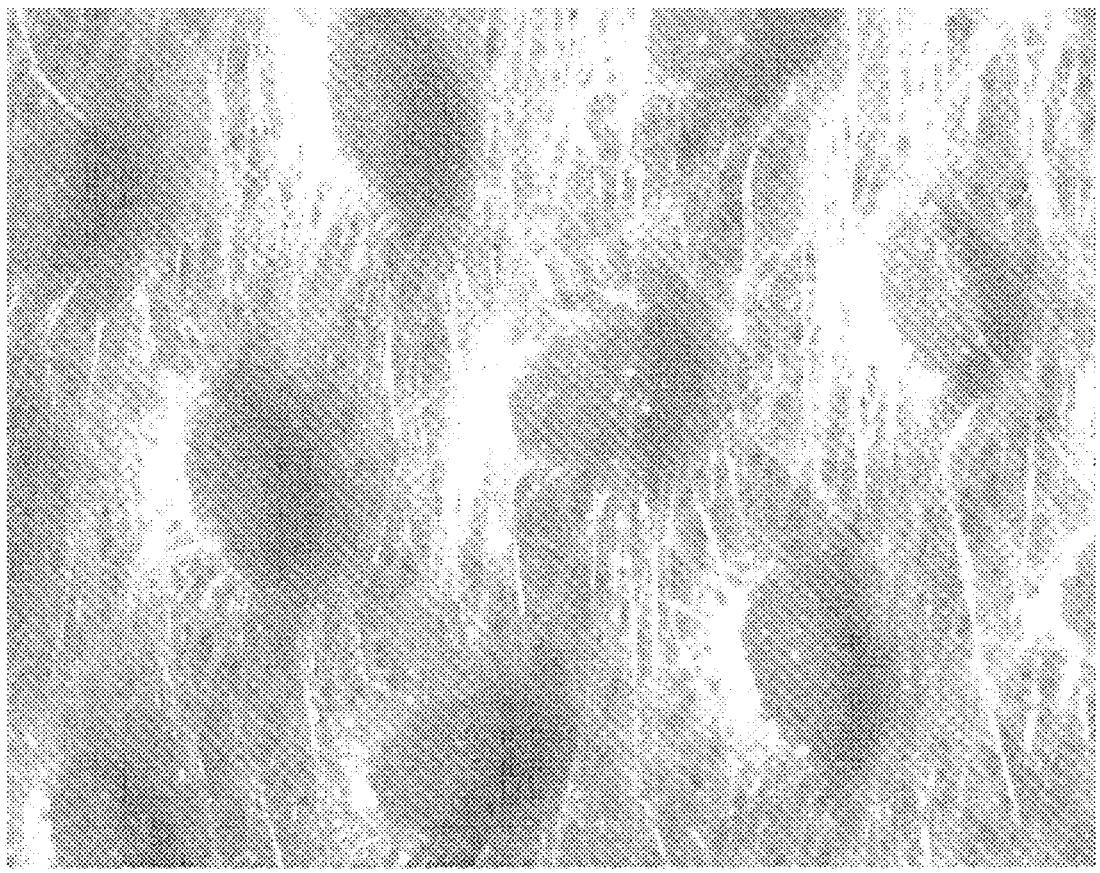
FIG. 1 is an enlarged illustration of a nonwoven material comprising spunbonded filaments. The oval areas are oval point bonded areas formed during the calendering process. The nonwoven material of FIG. 1 is not embossed.
Figure 2:
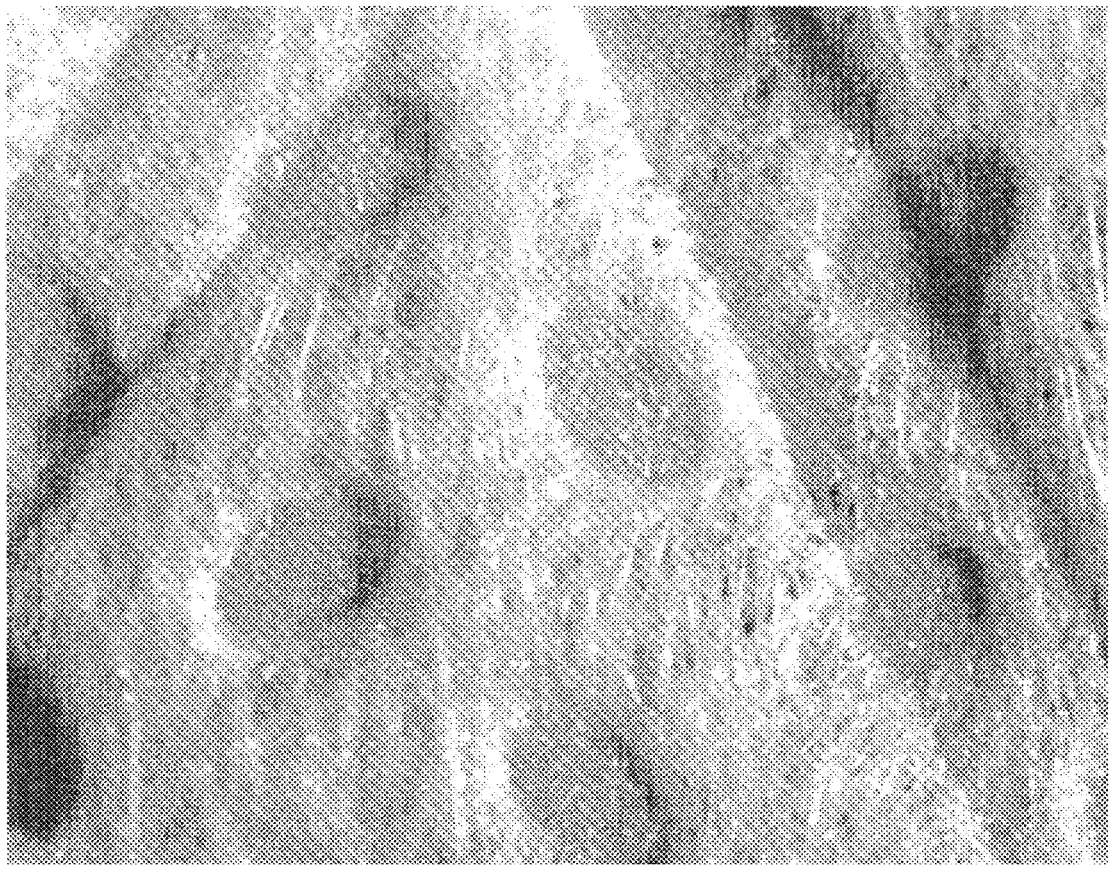
FIG. 2 is an illustration of the point bonded, nonwoven material of FIG. 1 after embossing. The embossing process formed two intersecting embossed regions, which are part of a larger hollow diamond pattern.

A preferred embodiment of the present invention comprises a nonwoven web having a regionally porous and hydrophilic structure that has been embossed. The nonwoven material can be an extruded web material. The embossed web material can advantageously provide one or more desirably enhanced properties including appearance, absorbency capacity, absorption rate, perception (three dimensional appearance) and softness as compared to conventional spunbonded nonwoven materials. The web material can advantageously be used as a fenestration material in a medical drape or as a medical drape.

Another preferred embodiment of the present invention comprises an extruded web material comprising a hydrophilically treated, nonwoven web of substantially continuous thermoplastic filaments that has been embossed. The embossing process provides the extruded web material with a regionally porous and hydrophilic structure and a desirably enhanced three-dimensional effect (perception). The embossing process also provides the extruded web material with a decorative bonding pattern and enhanced softness.

A third preferred embodiment of the present invention comprises a composite material produced by using the embossing process to join a first hydrophilically treated extruded web material to a second web material. The second web material can be a hydrophilically treated extruded web material. The embossing regionally joins the first and second web materials. The first and second web materials are not joined outside of the embossed regions. Advantageously, at least one of the extruded web materials comprises bicomponent filaments containing a low melting point polymer at the filament surface. The embossing process provides the composite material with a regionally porous and hydrophilic structure.

A fourth preferred embodiment of the present invention comprises an embossed nonwoven web or an embossed nonwoven composite laminated to a film.

A fifth preferred embodiment of the present invention comprises a nonwoven web material comprising thermoplastic staple fibers that has been embossed. The nonwoven web may be prepared by, for example, the wet laid or air laid processes. The embossing process provides the nonwoven web material with a regionally porous and hydrophilic structure and a three dimensional effect. The embossing process also provides the nonwoven web material with a decorative bonding pattern, superior perception and enhanced softness.

The starting web material useful in an embossed absorbent article process comprises discrete fibers such as staple fibers and/or substantially continuous filaments. The fibers and/or filaments of the web material are comprised of a thermoplastic polymer. The fibers and/or filaments can advantageously have a denier of about 0.5 to about 2.0 and can advantageously have a denier of about 1. The starting web material can have a grammage of about 15 grams per square meter (gsm) to about 300 gsm. The starting web material is advantageously an extruded web material comprising substantially continuous filaments formed by the spunbond process.

In a further embodiment a composite material comprising a spunbond, extruded web material joined to a layer comprising cellulosic materials may also be useful in an embossed absorbent article process. Such nonwoven webs made of cellulosic materials and/or non-cellulosic staple or continuous fibers and formed by the wet laid, air laid or carding processes may also be useful in an embossed absorbent article process.

A starting web material will typically be bonded to provide sufficient coherence of the constituent fibers or filaments so that the starting web material can be accumulated and handled in subsequent processes without substantially losing its sheet form. Any of the known processes can be used for bonding the starting web. For example, an extruded web material can be bonded by calendering between rotating heated rollers or by through air bonding in an oven. One of the rollers may be patterned, for example with spaced oval projections. The fibers or filaments disposed between the oval pattern and the smooth roll will be compressed and fused, or point bonded, as shown in FIG. 1. The fibers or filaments in the point bond area are regionally joined while the fibers or filaments outside the point bond area are substantially not bonded. Bonding can also be done by, for example, chemical bonding or hydraulic entangling. Bonding the starting web material to provide a "stiffer" material is advantageous for use in the embossing process.

Typically, nonwoven materials made from thermoplastic polymers are hydrophobic and lack the absorbency properties that are advantageous in fenestration products. The nonwoven material can, optionally, be treated with a surfactant or otherwise processed to impart a desired level of wettability and hydrophilicity. For example, the material can be surface treated with about 0.10 weight percent to about 0.50 weight percent, more desirably about 0.20 weight percent to about 0.40 weight percent of a commercially available surfactant. The surfactant can be applied by any conventional means, such as spraying, printing, brush coating or the like. If the surfactant is applied as an aqueous solution, the water carrier can be removed by, for example, application of heat to the material. The surfactant can be applied to the entire nonwoven material or can be selectively applied to particular sections of the nonwoven material. The thermoplastic nonwoven material can, optionally, be made wettable and hydrophilic by utilizing melt additives during formation of the thermoplastic filaments.

There are numerous other known in-process and post-process nonwoven web treatments that can be used to provide desired properties. For example, an antistatic material may be applied to the nonwoven after formation. The nonwoven material may additionally, or alternatively, be formulated so as to comprise any processes, components, materials, ingredients, adjuvants or species as long as the resulting material has suitable properties for use in an embossed absorbent article process.

Figures 3A, 3B:
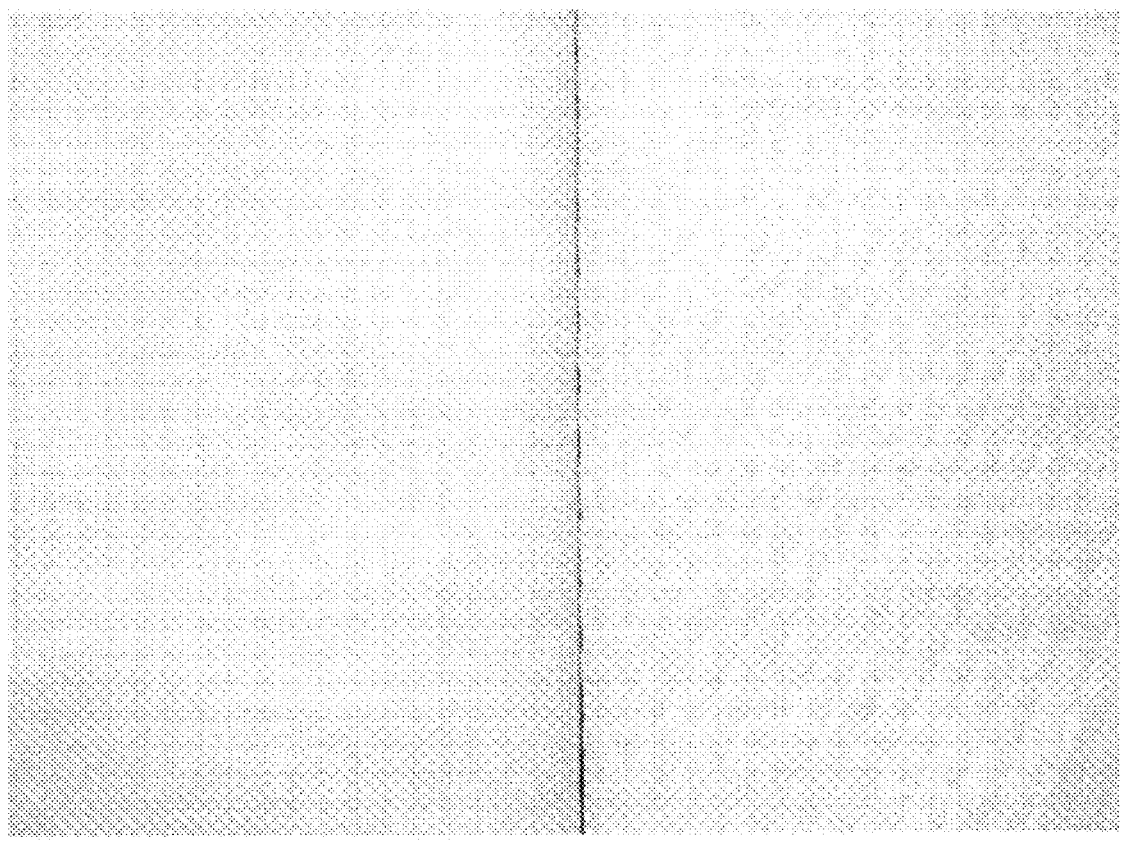
FIG. 3*a* is an illustration of the material of FIG. 1 at a different magnification. The oval areas are oval point bonded areas formed during the calendering process. The nonwoven material is not embossed.
FIG. 3*b* is an illustration of the nonwoven material of FIG. 3*a* after embossing with a hollow diamond pattern. The straight lines are embossed regions. The nonwoven material between the embossed lines is expanded.

The bonded starting web material is embossed. FIG. 3a illustrates an extruded web i.e. a spunbonded substrate and FIG. 3b illustrates a point bonded extruded web material that has further been embossed. The point-bonded areas can remain visible in the embossed regions and non-embossed areas as shown best in FIG. 4.

Figure 4:
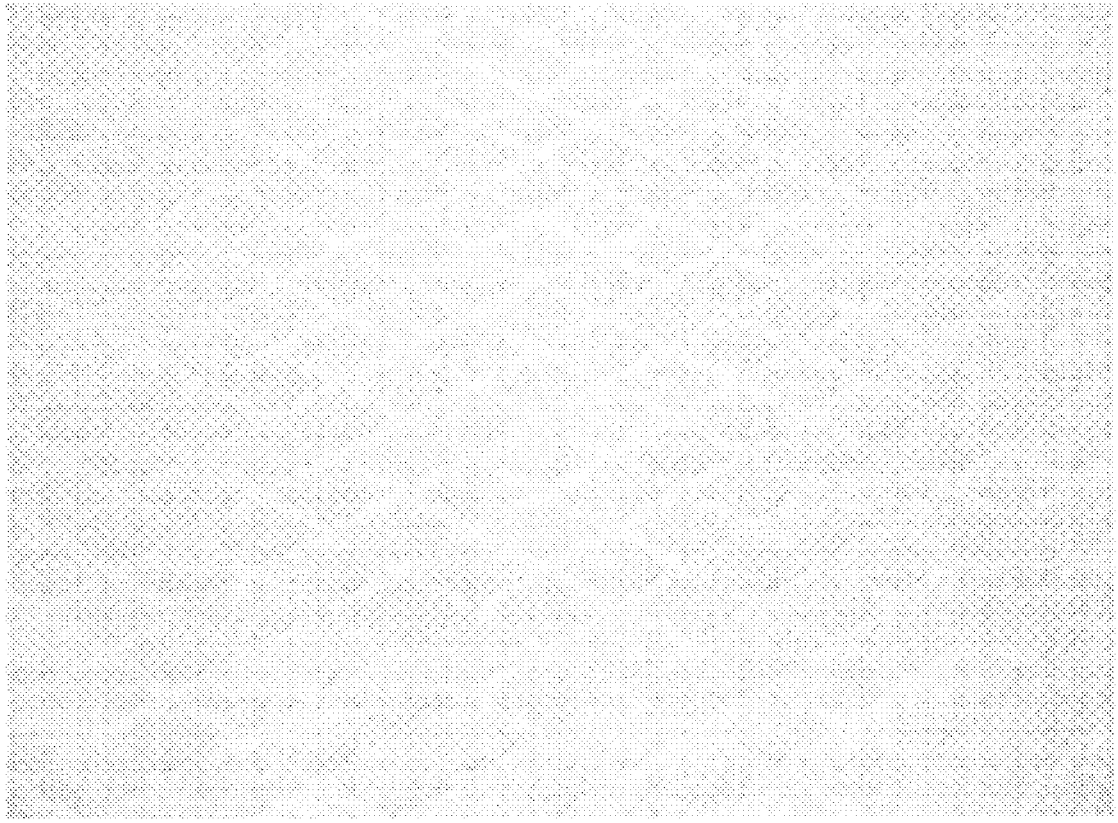
FIG. 4 is an illustration of the nonwoven material of FIG. 3*b* at a different magnification. The nonwoven material comprises spunbonded filaments. The oval areas are oval point bonded areas formed during the calendering process. The straight lines are embossed regions. The nonwoven material between the embossed lines is expanded.
Figure 5:
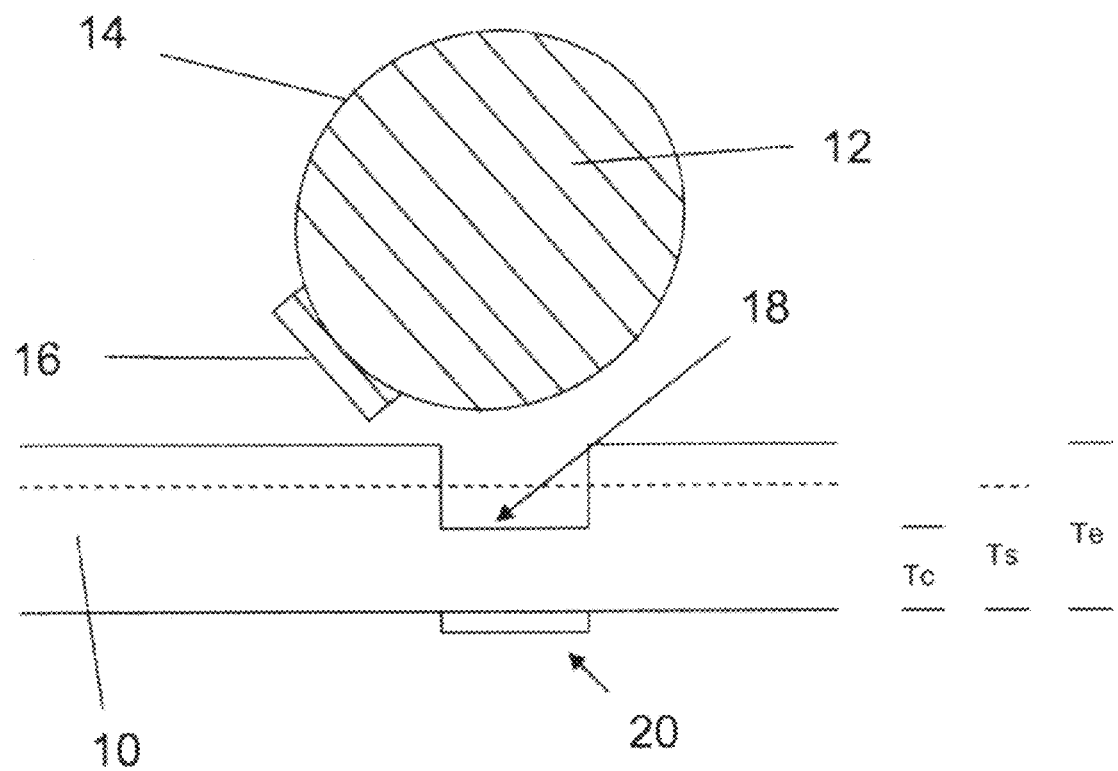
FIG. 5 is a schematic, cross-sectional illustration of one embodiment of an embossed extruded web material.

The preferred embossing process illustrated in FIG. 5 comprises passing the starting web material 10 between a rotating patterned steel roll 12 and a counter rotating resilient roll (not shown). Typically, the steel roll 12 is heated above ambient temperature and the resilient roll is not heated. The patterned steel roll 12 has a roll surface defining a roll diameter. Portions 14 of the roll surface are engraved to provide areas of the surface that are depressed below the diameter. For example, the steel roll 12 may define a surface comprising angularly intersecting lines. The portions 14 of the roll surface between the angularly intersecting lines are depressed below this surface. This example will provide a spaced, hollow diamond pattern such as shown in FIG. 4 when applied to a sheet material. The embossing process imparts heat and pressure to localized regions of the starting web material 10 adjacent the patterned roll surface.

The starting web material 10 having an initial thickness Ts is fed between the counter rotating patterned steel roll 12 and resilient roll. As shown best in FIG. 5 fibers or filaments in the starting web material 10 adjacent the patterned roll surface 16 are compressed and partially fused to form an embossed portion 18 having a compressed thickness Tc that is less than Ts. The thermoplastic filaments in the embossed portions 18 are typically partially fused and may exhibit changes in filament morphology such as flattening and/or flow of the thermoplastic filament material. The compression may displace a portion 20 of the web material adjacent the resilient roll (not shown in FIG. 5) below the surface of the web material. The resilient roll hardness, space between the rolls, nip pressure, steel roll temperature and line speed are adjusted so that the thermoplastic filaments adjacent the roll engraved or depressed areas 14 are separated and raised above the surface of the starting web material 10 to form an expanded portion having an expanded thickness Te greater than Ts. There can be some fusion of the thermoplastic filaments in the expanded areas, however there is typically no substantial change of filament morphology or flow of the filament thermoplastic polymer.

The embossed web material defines a cross sectional "peak and valley" structure. The fibers or filaments in the embossed web material define a three-dimensional structure between the outer surfaces of the web material. The fibers or filaments in the expanded or peak areas define a structure having a comparatively increased void volume compared to the non-embossed web material.

The embossing process is not interchangeable with a calendering process. The calendering process typically uses a first heated smooth steel roller and a second, heated engraved steel roller to impart heat and pressure to localized bond areas in the nonwoven web material. The thermoplastic filaments in these localized areas are compressed below the surface of the web material and will melt and flow under the imparted heat and pressure. As the web material passes beyond the rollers the melted thermoplastic solidifies, joining the compressed filaments in these localized areas. The compressed web material thickness (Tc) is less than the initial thickness (Ts) of the starting web material. The fused thermoplastic fibers are stiff and the web material has little volume between filaments in the localized areas. The web material maintains its initial thickness (Ts) in areas that have not been compressed. There is no increase in void volume in areas that have not been compressed.

Figure 6:
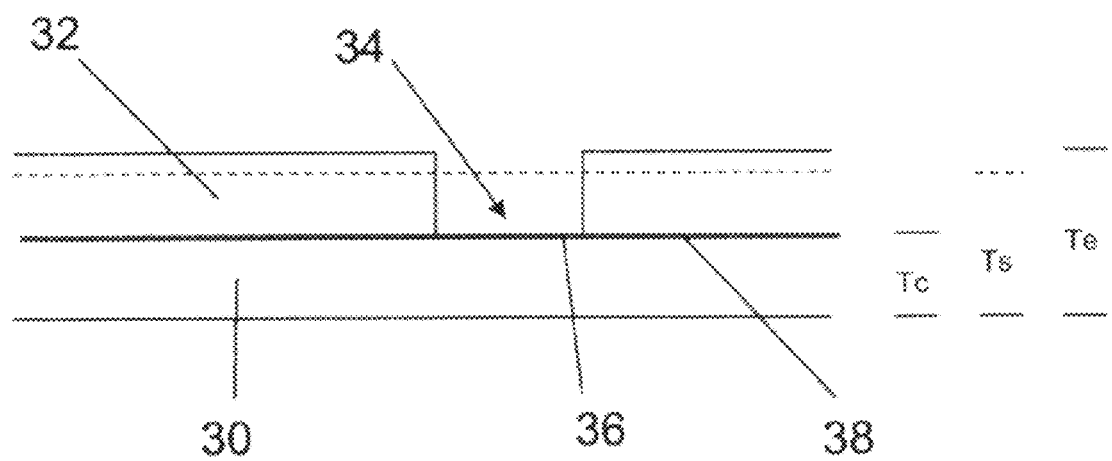
FIG. 6 is a schematic, cross-sectional illustration of one embodiment of an embossed composite material comprising a first extruded web material overlying a second extruded web material.

In some embodiments such as shown schematically in FIG. 6 two or more web materials 30 and 32 are joined to provide an embossed composite nonwoven material. Each web material in this embodiment is bonded, for example by point bonding, prior to embossing. The fibers or filaments, or portions thereof, in the embossed portions 34 are at least partially fused within each layer and also with fibers or filaments of the other layers 30 and 32. The fused fibers or filaments act as discrete bonding regions 36 between the layers 30 and 32. The fibers or filaments in the expanded portions are an unbonded area 38 and are not substantially fused with the fibers or filaments in that layer or any other layer. In this embodiment it is advantageous for at least one of the web material layers to comprise filaments having a thermoplastic component with a melting point lower than the other thermoplastic components used in the web material layers. In some variations one web material layer can comprise bicomponent filaments having a higher melting point polyethylene terephthalate core and a lower melting point polyethylene sheath.

The expanded or peak portions of the embossed areas of the composite nonwoven material define a structure within each layer having a comparatively increased void volume compared to the non-embossed composite web material or the compressed portions. Additionally, there are void volumes defined between the adjacent interior surfaces of each layer. These inter-surface void volumes are believed to be in fluid communication with the inter-layer void volumes.

In a yet further embodiment of the invention the embossed material can be laminated to a non-fibrous film to form a composite nonwoven/film laminate. Lamination of the film to the embossed material may be performed by using any known lamination process. For example, a molten film can be extruded over the embossed material or the film can be adhesively bonded to the embossed nonwoven.

Having generally described the invention, the following examples are included for purposes of illustration so that the invention may be more readily understood and are in no way intended to limit the scope of the invention unless otherwise specifically indicated.

The starting web material was a spunbonded nonwoven having a grammage of about 50 gsm. The starting web material was prepared from polypropylene filaments of about 1.6 denier. The laid down filaments were calendered at a line speed of about 350 feet per minute (1.5 m/s) and a nip pressure of about 550 pounds per linear inch (0.96 kN/cm) between a first rotating heated smooth steel roll and a second rotating heated engraved roll. The engraved roll had a series of spaced ovals laid out in a repeating pattern. The oval pattern provided bonding over about 20% of the starting web material area. FIGS. 1 and 3a show the point bonded starting web material.

EXAMPLE 1

Samples of the starting web material were embossed using a top, heated metal embossing roll having a diamond pattern under varied conditions for each sample. The embossing roll diameter was about 15 inches (38 cm). The embossing roll had a series of diamond outlines in a repeating pattern providing embossing over about 20% of the web material area. The opposing resilient roll was a rubber composition having a 45 Shore D hardness. The extruded web material was embossed under the conditions shown in Table 1.

TABLE 1

| sample | embossing roll setting (° F.)/(° C.) | embossing roll surface temp (° F.)/(° C.) | nip pressure (psi)/(MPa) | line speed (feet/min)/(m/s) | Remarks* |
|---|---|---|---|---|---|
| 1 | 420/216 | 300/149 | 700/4.8 | 300/1.5 | 5 |
| 2 | 430/221 | not recorded | 700/4.8 | 500/2.5 | 5 |
| 3 | 420/216 | 280-290/138-143 | 700/4.8 | 400/2.0 | 5 |
| 4 | 420/216 | 275-285/135-141 | 700/4.8 | 500/2.5 | 4 |
| 5 | 420/216 | 285-290/141-143 | 700/4.8 | 430/2.2 | 68" wide web, 4 |
| 6 | 420/216 | 290-295/143-146 | 700/4.8 | 400/2.0 | 62" wide web, 4 |

1 flat
3 somewhat 3-D effect
5 outstanding 3-D effect

The starting web material and embossed nonwoven material samples of Example 1 were tested. The 'embossed' results are an average of the results from samples 1 to 6. The results are summarized in Table 2.

TABLE 2

|  | non-embossed | embossed |
|---|---|---|
| width (inches)/(cm) | 68/172.7 | 68.2/173.2 |
| grammage (gsm) | 51.79 | 51.85 |
| thickness, one layer (micron) | 350 | 385 |
| $H_2O$ drop, 100 µL (seconds) | 1.5 | 1.8 |
| absorbency (%) | 312 | 315 |

The following test methods were used in this application and each of the methods is incorporated by reference herein. The test method used to measure "absorbency" is Ahistrom™ 107 Rev. 0. The test method used to measure $H_2O$ drop is TAPPI T-4320M-94.

EXAMPLE 2

A portion of the starting web material was embossed using the same equipment as Example 1 to provide sample 7. The starting web material and embossed nonwoven material (sample 7) were tested. The results are summarized in Table 3.

TABLE 3

|  | Starting web material non-embossed | Sample 7 embossed |
|---|---|---|
| absorbency (%) | 240 | 241 |
| Perception* | 1 | 4 |
| perception after aging in roll form* | 1 | 4 |
| Handle-o-meter, grams at 10 mm gap | 44 | 34 |

A handle-o-meter was used to measure the bending rigidity of the starting web material and embossed nonwoven material. Handle-o-meter is a measurement of the force required to push a fabric into a slotted opening of measured gap (5 mm, 10 mm or 20 mm). A gap of 10 mm was used. The bending rigidity in the machine direction (MD) (the longitudinal direction of the laminate web) is measured by orienting the slot of the handle-o-meter in the cross-machine direction (CD) and the bending rigidity in the cross-machine direction is measured by orienting the slot of the handle-o-meter in the machine direction.

After embossing Sample 7 had a desirably improved perception (three dimensional appearance) as compared to the non-embossed starting web material. The desirably improved perception was maintained after the sample was held in a roll form.

EXAMPLE 3

The embossed material of example 3 is a composite nonwoven material comprising a first 25 gsm extruded web material prepared from spunbonded polypropylene filaments regionally joined to a second 25 gsm extruded web material comprising spunbonded polypropylene filaments. The composite material was joined by the embossing process. The composite nonwoven material was embossed using the same equipment as example 1 to provide sample 8. The composite embossed nonwoven material (sample 8) was tested. The results for sample 8 are summarized in Table 4.

TABLE 4

|  | sample 8<br>composite, embossed material |
|---|---|
| absorbency (%) | 353 |
| Perception* | 4 |
| perception after aging in roll form* | 4 |
| Handle-o-meter, grams at 10 mm gap | 35.5 |

EXAMPLE 4

The embossed material of example 4 (sample 9) is a composite nonwoven material comprising a first 25 gsm extruded web material comprising spunbonded polypropylene filaments regionally joined to a second 25 gsm extruded web material comprising spunbonded bicomponent filaments having a polyethylene sheath and a PET core. The first and second extruded web materials were joined by embossing at similar conditions as that in Example 1. Results for sample 9 are shown in Table 5.

TABLE 5

|  | sample 9<br>composite, embossed material |
|---|---|
| absorbency (%) | 360 |
| Perception* | 4 |
| perception after aging in roll form* | 4 |

Sample 9 showed significant improvements in absorption capacity compared with a single layered 50 gsm embossed SB material. Visual evaluation indicated that embossing the Example 4 material provided an advantageous three-dimensional effect (perception). The three-dimensional effect and other improved properties remained even after prolonged compressing conditions such as storage of the nonwoven material in roll form.

In general, the compositions of the invention may be alternately formulated to comprise, consist of, or consist essentially of, any appropriate components herein disclosed. The compositions of the invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

When the word "about" is used herein it is meant that the amount or condition it modifies can vary some beyond that so long as the advantages of the invention are realized. Practically, there is rarely the time or resources available to very precisely determine the limits of all the parameters of ones invention because to do would require an effort far greater than can be justified at the time the invention is being developed to a commercial reality. The skilled artisan understands this and expects that the disclosed results of the invention might extend, at least somewhat, beyond one or more of the limits disclosed. Later, having the benefit of the inventors disclosure and understanding the inventive concept and embodiments disclosed including the best mode known to the inventor, the inventor and others can, without inventive effort, explore beyond the limits disclosed to determine if the invention is realized beyond those limits and, when embodiments are found to be without any unexpected characteristics, those embodiments are within the meaning of the term about as used herein. It is not difficult for the artisan or others to determine whether such an embodiment is either as expected or because of either a break in the continuity of results or one or more features that are significantly better than reported by the inventor, is surprising and thus an unobvious teaching leading to a further advance in the art.

While preferred embodiments of the foregoing invention have been set forth for purposes of illustration, the foregoing description should not be deemed a limitation of the invention herein. Accordingly, various modifications, adaptations and alternatives may occur to one skilled in the art without departing from the spirit and scope of the present invention.

The invention claimed is:

1. A nonwoven medical drape fabric comprising a nonwoven web material layer having thermoplastic polymer fibers or filaments, wherein the nonwoven web material layer has an embossed pattern including compressed portions with a compressed thickness Tc and expanded portions, each expanded portion having an expanded thickness Te, wherein the expanded portions have an increased void volume compared to the original nonwoven web material layer of thickness Ts prior to embossing, wherein the nonwoven material layer is formed by:
   embossing the original nonwoven web material layer by passing the original nonwoven web material layer between a rotating patterned steel roll with engraved depressed areas and a counter rotating resilient roll, and wherein the nonwoven medical drape fabric is a fenestration material adjacent a fenestration defined in a medical drape.

2. The nonwoven medical drape fabric of claim 1 further comprising, before the step of embossing, air-laying, wet-laying or carding staple fibers or extruding substantially continuous filaments to form the nonwoven web material layer.

3. The nonwoven medical drape fabric of claim 1 further comprising, before the step of embossing, extruding the nonwoven web material layer from substantially continuous spunbonded filaments.

4. The nonwoven medical drape fabric of claim 1 further comprising, before the step of embossing, bonding the nonwoven web material layer to maintain a sheet form.

5. The nonwoven medical drape fabric of claim 4 wherein the bonding includes using at least one of calendaring, air bonding in an oven, chemical bonding and hydraulic entangling.

6. The nonwoven medical drape fabric of claim 1 further comprising joining the nonwoven web material layer to at least one other nonwoven web material layer to form a composite nonwoven web material.

7. The nonwoven medical drape fabric of claim 6 further comprising, before the step of embossing, treating or hydrophilically treating at least one of the nonwoven web material layer and a second nonwoven web material.

8. The nonwoven medical drape fabric of claim 6 wherein said other nonwoven web material layer includes cellulosic material.

9. The nonwoven medical drape fabric of claim 1 wherein the expanded portion is formed by separating and raising thermoplastic filaments above a surface of the web material layer in regions of the layer that are adjacent the embossed portion formed as the layer is passed between the steel roll and the resilient roll of the roll.

10. The nonwoven medical drape fabric of claim 9 further comprising adjusting at least one of the resilient roll hardness, space between the rolls, nip pressure, steel roll temperature and line speed to separate and raise the thermoplastic filaments.

11. The nonwoven medical drape fabric of claim 9, further comprising heating the rotating patterned steel roll.

12. The nonwoven medical drape fabric of claim 1 further comprising a film laminated to the nonwoven web material layer.

13. The nonwoven medical drape fabric of claim 11 wherein the surface temperature of the patterned steel roll is between 135° C. and 149° C.

14. The nonwoven medical drape fabric of claim 1 further comprising, before the step of embossing, treating or processing the nonwoven web material layer, at least partially, to impart hydrophilicity to the material layer.

15. The nonwoven medical drape fabric of claim 1 wherein the nonwoven web material layer is a first nonwoven web material layer and the medical drape fabric also includes a second nonwoven web material layer of thermoplastic polymer material.

16. The nonwoven medical drape fabric of claim 15 wherein said second nonwoven web layer is a hydrophilically treated extruded web.

17. The nonwoven medical drape fabric of claim 15 wherein the at least one of the first and second nonwoven material layers includes a bicomponent filament.

18. The nonwoven medical drape fabric of claim 17 wherein the bicomponent filament comprises at least one of a polyethylene and polyethylene terephthalate.

19. The nonwoven medical drape fabric of claim 15 wherein the nonwoven material web or layer is regionally joined at a plurality of spatially separated regions to said nonwoven web of thermoplastic polymer material having an embossing pattern with a regionally porous and hydrophilic structure.

20. The nonwoven medical drape fabric of claim 15 wherein said nonwoven material web material layer is formed by at least one of a wet laid, an air laid, an extrusion of continuous filaments and a carding process.

21. The nonwoven medical drape fabric of claim 15 wherein said nonwoven web material layer comprises cellulosic materials.

22. The nonwoven medical drape fabric of claim 15 wherein said nonwoven web material layer comprises at least one of thermoplastic staple fibers and continuous filaments.

23. The nonwoven medical drape fabric as in claim 1 having a basis weight in the range of 15 gsm to 300 gsm.

24. The nonwoven medical drape fabric as in claim 1 including fibers or filaments having a denier in the range of 0.5 to 2.0.

25. The nonwoven medical drape fabric of claim 1 wherein the nonwoven web material layer includes spunbonded polypropylene filaments.

26. The nonwoven medical drape fabric of claim 1 wherein the nonwoven web material layer includes bicomponent filaments.

27. A nonwoven medical drape fabric comprising:
a nonwoven web material layer having spunbonded thermoplastic polymer filaments, wherein the nonwoven web material layer has an embossed pattern including compressed portions having a compressed thickness Tc and expanded portions having an expanded thickness Te, wherein the expanded portions have an increased void volume compared to the original nonwoven web material layer of thickness Ts, wherein the nonwoven medical drape fabric is a fenestration material adjacent a fenestration defined in a medical drape and the nonwoven web material layer is formed by:
passing the original nonwoven web material layer having the thickness Ts between a rotating patterned steel roll with engraved depressed areas and a counter rotating resilient roll.

28. The nonwoven medical drape fabric of claim 27 wherein the nonwoven web material is a first layer and the medical drape fabric further comprises a second layer of a nonwoven web material, wherein at least one of the first layer and the second layer includes bicomponent fibers or filaments.

29. The nonwoven medical drape fabric of claim 27 wherein said nonwoven web material layer is a hydrophilically treated extruded web material.

30. The nonwoven medical drape fabric of claim 27 including a surface of the nonwoven web material layer and a film laminated to the surface.

31. A nonwoven medical drape fabric comprising a nonwoven web material layer having thermoplastic polymer fibers or filaments, wherein the nonwoven web material layer has a pre-embossing thickness of Ts and a post-embossing thicknesses of Tc and Te, wherein the Tc thickness corresponds to one or more regions of the layer compressed by embossing and the Te thickness corresponds to one or more regions of the layer expanded by embossing, and wherein thickness Te is greater than Tc and the thickness Ts is smaller than Te, wherein the nonwoven medical drape is a fenestration material adjacent a fenestration defined in a medical drape.

* * * * *